(12) United States Patent
Von Stenglin (10) Patent No.: US 11,344,819 B2
(45) Date of Patent: May 31, 2022

(54) RAPID EVAPORATOR ARRANGEMENT WITH RAPID EVAPORATOR, AND OPERATING METHOD

(71) Applicant: Metall + Plastic GmbH, Radolfzell (DE)

(72) Inventor: Christoph Von Stenglin, Radolfzell (DE)

(73) Assignee: Metall + Plastic GmbH, Radolfzell (DE)

( * ) Notice: Subject to any disclaimer, the term of this patent is extended or adjusted under 35 U.S.C. 154(b) by 0 days.

(21) Appl. No.: 15/552,304

(22) PCT Filed: Feb. 18, 2016

(86) PCT No.: PCT/EP2016/053482
§ 371 (c)(1),
(2) Date: Nov. 14, 2017

(87) PCT Pub. No.: WO2016/131931
PCT Pub. Date: Aug. 25, 2016

(65) Prior Publication Data
US 2018/0117492 A1 May 3, 2018

(30) Foreign Application Priority Data
Feb. 20, 2015 (DE) ..................... 10 2015 102 491.8

(51) Int. Cl.
*B01B 1/00* (2006.01)
*A61L 2/20* (2006.01)

(52) U.S. Cl.
CPC .............. *B01B 1/005* (2013.01); *A61L 2/208* (2013.01); *A61L 2202/11* (2013.01); *A61L 2202/21* (2013.01)

(58) Field of Classification Search
CPC ...... B01B 1/005; A61L 2/208; A61L 2202/21; A61L 2202/11
See application file for complete search history.

(56) References Cited

U.S. PATENT DOCUMENTS 4,797,255 A * 1/1989 Hatanaka .................. A61L 2/20
422/28
6,649,591 B2 11/2003 Lai
(Continued)

FOREIGN PATENT DOCUMENTS

| CN | 200943844 Y | 9/2007 |
| DE | 60300820 T2 | 3/2006 |

(Continued)

OTHER PUBLICATIONS

English translation of WO2011076400 (Year: 2011).*
International search report for application No. PCT/EP2016/053482 dated Apr. 5, 2016.

*Primary Examiner* — Regina M Yoo
(74) *Attorney, Agent, or Firm* — Bachman and Lapointe PC; George Coury (57) ABSTRACT

A device for generating a decontaminating agent vapor, in particular hydrogen peroxide vapor, comprising a single- or multipart evaporator body (1); a heating device for heating the evaporator body (1); at least one supply channel, preferably multiple supply channels, for supplying a liquid decontaminating agent to be evaporated, in particular hydrogen peroxide, to at least one of multiple blind holes (7, 8, 9, 10) arranged in the evaporator body (1); and a flow channel (2) which is arranged above the upper blind holes edges (11, 12, 13, 14) of the blind holes (7, 8, 9, 10) and which connects a carrier medium inlet (3) to an outlet (4) in a gas-conductive manner for a gaseous carrier medium, in particular air, in order to discharge the decontaminating agent vapor through the outlet (4) in a flow direction of the carrier medium.

(Continued)

According to the invention, at least two of the blind holes (7, 8, 9, 10), preferably all of the blind holes (7, 8, 9, 10), are fluidically connected together at a distance from the respective upper blind hole edges (11, 12, 13, 14).

19 Claims, 4 Drawing Sheets

(56) References Cited

U.S. PATENT DOCUMENTS

| | | | |
|---|---|---|---|
| 8,428,447 B2 | 4/2013 | Von Stenglin | |
| 9,638,368 B2* | 5/2017 | Kriens, Jr. | F16L 55/18 |
| | | | 285/197 |
| 9,783,881 B2* | 10/2017 | Liang | C23C 14/0623 |
| 2013/0056104 A1* | 3/2013 | Kriens, Jr. | F16L 55/168 |
| | | | 138/99 |
| 2013/0069361 A1* | 3/2013 | Cai et al. | F16L 37/138 |
| | | | 285/133.21 |

FOREIGN PATENT DOCUMENTS

| | | |
|---|---|---|
| DE | 60203603 T2 | 5/2006 |
| DE | 102005030822 A1 | 1/2007 |
| DE | 102006006095 A1 | 5/2007 |
| EP | 1193462 A2 | 4/2002 |
| EP | 1738777 A2 | 1/2007 |
| WO | 2006108796 A1 | 10/2006 |
| WO | 2011076400 A1 | 6/2011 |

\* cited by examiner

RAPID EVAPORATOR ARRANGEMENT WITH RAPID EVAPORATOR, AND OPERATING METHOD

BACKGROUND OF THE INVENTION

The invention relates to a device (rapid vapor generator) for generating decontamination agent vapor, in particular hydrogen peroxide vapor, comprising a single- or multipart evaporator body, a heating device for heating the evaporator body as well as at least one supply channel, preferably multiple supply channels for supplying a liquid decontaminating agent to be evaporated, in particular hydrogen peroxide, to at least one of multiple blind holes arranged in the evaporator body, and to a flow channel arranged above upper blind hole edges and which connects an inlet for a gaseous carrier medium, in particular air, to an outlet in a gas-conducting manner, for discharging the decontaminating agent vapor through the outlet in a flow direction of the carrier medium.

The invention further relates to a preferably pharmaceutical arrangement, comprising a space to be decontaminated, in particular an isolator and/or a port and a device for generating decontamination agent vapor.

Furthermore, the invention relates to a method for operating a device for generating decontaminating agent vapor.

For decontaminating insulators and/or locks, hydrogen peroxide vapor, due to the high reactivity thereof, is used in the pharmaceutical industry. This vapor is obtained by evaporating an aqueous hydrogen peroxide solution. For minimizing the risk of explosions when evaporating hydrogen peroxide-containing solutions, so-called rapid evaporators (rapid vapor generators) are used with the objective to continuously abruptly (rapid) evaporate small amounts of hydrogen peroxide-containing liquid. Boiling greater amounts of hydrogen peroxide-containing liquid is not permitted due to the above-mentioned explosion risk. The difficulty in evaporating small amounts of hydrogen peroxide-containing liquid, in particular aqueous solutions, is the formation of liquid drops "dancing" on a hot evaporator surface which interfere with the efforts of a rapid evaporation.

A hydrogen peroxide vapor generator is known from DE 10 2006 006 095 A1 and comprises a planar evaporator surface. Here, the above-mentioned "dancing" formation of droplets may occur.

An alternative rapid evaporator (flash evaporator) is known from EP 0 927 159 B1and characterized by evaporator channels arranged in hydraulic communication in an evaporator body. The structure is relatively complex.

Reference is made to DE 602 03 603 T2 or DE 603 00 820 T2 regarding further prior art.

DE 2005 030 822 A1 discloses a hydrogen peroxide evaporator with a pot-like housing and an evaporator body which comprises one single, extensive evaporator surface, wherein the heat supply in the decontamination agent is effected exclusively from below. The known evaporator seems to be in need of improvement regarding its evaporating rate and regarding the prevention of "dancing" decontamination agent droplets. In addition, DE 2005 030 822 A1 discloses to connect multiple evaporators with a vessel to be sterilized via a respective line to increase the amount of decontamination vapor. The overall evaporator costs thus result many times. Additionally, a plurality of vapor lines must be guided into the space to be vaporated, which is problematic in small spaces due to a lack of space. Additionally, a plurality of sealings has to be provided.

CN 2009 43844 Y discloses an evaporator for water. The known evaporator comprises an evaporator body with a plurality of small openings. A single intake channel is commonly assigned to these holes, the channel being arranged centrally above the evaporator body. In order that the plurality of small openings can contribute to the evaporation, a sufficiently great amount of liquid must be supplied through the only supply channel which in turn would run counter a spontaneous rapid evaporation of decontamination agents. In practice, a dangerous vaporization of decontamination agent would occur. Therefore, the known evaporator is not suitable for evaporating decontamination agent.

EP 1 738 777A1 discloses an evaporator for a sterilization apparatus having four supply channels, through which liquid decontamination agent is sprayed on a heatable plate. The evaporator surface can comprise depressions, for example in the shape of hemispheres.

All rapid evaporators mentioned above are characterized by a comparably complex structure and/or an evaporation rate in need of improvement.

In EP 2 448 602 B1, a rapid evaporator significantly improved compared to the above-mentioned prior art, which stands out due to the fact that in the single- or multipart evaporator body of the rapid evaporator multiple blind holes are provided, to which in each case at least one of the supply channels is assigned and wherein the supply channels are configured in such a way that the decontaminating agent to be evaporated can be supplied dropwise directly to the blind holes. This improved rapid evaporator stands out due to a high evaporating rate and "dancing" liquid decontaminating agent drops are widely prevented within the evaporator as the evaporation takes place within circumferentially closed blind holes in the evaporator body. The improved rapid evaporator has proved of value—however, there are efforts to increase the selection safety, in particular in the case where one of the supply channels might fail.

SUMMARY OF THE INVENTION

In view of the above-mentioned prior art, the object underlying the invention is to provide a rapid evaporator for decontamination agents which is characterized by high operational safety and, at the same time, a high vaporization rate with at least widely preventing "dancing" decontaminating agent drops.

Further, the object is to provide a (decontamination) arrangement with a space to be decontaminated and a correspondingly improved rapid evaporator as well as an optimized operating method for a rapid evaporator according to the invention.

This object is achieved, regarding the rapid evaporator with the features disclosed herein, i.e. in a generic rapid evaporator in that at least two of the blind holes, preferably all blind holes, are connected to one another in a fluidic manner at a distance to their respective upper blind hole edges.

Regarding the arrangement, the object is achieved with the features disclosed herein and regarding the operating method also with the features disclosed herein, i.e. in a generic method in that liquid decontamination agent supplied in one of the blind holes flows into one of the blind holes and there is evaporated into decontamination agent vapor.

Advantageous developments of the invention are provided in the dependent claims. All combinations of at least two features disclosed in the description, the claims and/or the figures fall within the scope of the invention.

To avoid repetitions, features disclosed according to the device are considered to be disclosed according to the method and be claimable. Similarly, features disclosed according to the method are considered to be disclosed according to the device and be claimable.

The idea underlying the invention is to connect at least two blind holes arranged in the evaporator body at a distance to the blind hole upper surfaces, i.e. below a circumferentially closed section of each blind hole in a fluidic manner, preferably by interconnected, so that the liquid decontamination agent supplied in one of the blind holes can flow in at least one neighboring blind hole at a distance to the flow channel formed above the blind holes. In other words, at a distance to the flow channel in which the decontamination agent vapor originating in the blind holes and ascending upward with the help of a carrier medium, in particular air, is transferred into the space to be decontaminated, at least one connecting channel is to be arranged between two blind holes in the evaporator body which enables a distribution of liquid decontamination agent between at least two blind holes. Thereby, the evaporator capacity of a blind hole in which the liquid decontamination agent is interrupted, for example due to a blocked supply channel, can further be used to evaporate liquid decontamination agent flowing out of at least one other blind hole and thus ensure a continuous supply of the space to be decontaminated with a high decontamination agent vapor volume flow. In this way, the rapid evaporator according to the invention (flash evaporator) ensures a high evaporating rate due to the provision of the blind holes in the evaporation body and furthermore is characterized by an increased fail-safety, as even in case of one or multiple supply lines failing, a great evaporator surface is at disposal. In a rapid evaporator designed according to the concept of the invention, a great amount of heat can be supplied to the liquid decontamination agent to be evaporated, preferably supplied dropwise, namely not only from above but also through radiant heat from the circumferential walls of the blind holes. Preferably, the liquid decontamination agent to be evaporated is an aqueous solution of hydrogen peroxide, particularly preferably a 35% to 50% solution.

An embodiment is particularly preferred in which in each case at least one of the supply channels is assigned to the blind holes and the supply channels are arranged in such a way that the liquid decontamination agent to be evaporated can be supplied directly in each of the blind holes, in particular dropwise. The configuration according to the invention of the rapid evaporator, however, also for an alternative design variant, simpler in structure and more cost-effective, in which individual supply channels are intentionally omitted, i.e. in which not all blind holes have a supply channel assigned thereto but at least one of the blind holes connected to one another in a fluidic manner and the distribution of the liquid decontamination agent is not or not exclusively effected via the supply channels but at least partly via the liquid-conductive connections below the flow channel. In such an embodiment, "dancing" drops are prevented due to the distribution of the liquid decontamination agent and the high evaporating capacity of the blind holes is made use of.

It is particularly expedient, irrespective of the selection of one of the above-described modification variants, if the present supply channels, are guided through the flow channel, preferably perpendicular to the longitudinal extent of the flow channel, for example in the form of injection needles, and end below the respective upper blind hole edge within the respective blind hole, preferably in such a way that the liquid decontamination agent exiting from the supply channels can drop directly down on the blind hole bottom in case of a vertical free fall. By penetrating or permeating the flow channel with the at least one supply channel, carrying along of the liquid decontamination agent drop with the carrier medium in the direction of the outlet can definitely be reliably prevented.

In view of the specific configuration of the blind holes, there are different options. It is preferred if the blind holes extend larger in depth than to the sides. In other words, the maximum diameter of the blind holes in a circumferentially closed region, i.e. above a fluidic connection, is greater than the respective extension in depth. A cylindric contouring of the circumferentially closed region above the fluidic connection has proven particularly advantageous.

As already mentioned, the blind holes are characterized by a section having a circumferentially closed shell surface, and adjoins the upper blind hole edge. Below this circumferentially closed shell surface, the fluidic connection according to the invention is then provided.

Preferably, the blind holes are arranged in a solid block (evaporator block) and further preferably produced as bores, whereby an extremely simple and effective structure of the evaporator device is ensured.

It is particularly expediently, to configure and/or control the heating device in such a way that the device heats the evaporator body to a temperature of a temperature range of between 100° C. and about 140° C. at least in the region of the blind holes. More particularly preferably, the temperature during evaporating operation is about 120° C. or less, to optimally prevent the drops not immediately evaporating on the evaporator surface, i.e. on the blind hole bottom.

Particularly preferably is an embodiment of the rapid evaporator in which the fluidic connection between at least two blind holes is configurated in such a way that the connection connects the lowest regions, i.e. the blind hole bottoms with a straight (planar, preferably horizontal) connection plane—in other words, the lowest regions of the blind holes connected to one another in a fluidic manner and the base or the bottom of the connection, in particular of a connection channel, are located in a common plane to ensure an even distribution of the liquid decontamination agent and to prevent an accumulation in the fluidic connection or in the connection channel. By the fluidic connection configured as described above, it is also ensured that the liquid does not have to overcome a step upward to get into the region of the fluidic connection or the connection channel.

As already indicated, the liquid-conductive connection between at least two blind holes is preferably configured as a circumferentially closed channel, arranged at distance to the flow channel, in the evaporator body. It is particularly preferably, if at least one of the blind holes is connected to another or neighboring blind hole in a fluidic manner via in each case such a connection channel. Here, the connection channel bridges over the distance between two neighboring blind holes in the type of a tunnel below the flow channel.

Instead of realizing individual connection channels between neighboring blind holes, it is alternatively also conceivable to establish a common connection space which is preferably not interrupted by perpendicular or vertical pillars arranged therein—thereby, the directly heated base and thus the effective evaporator surface can be increased.

Irrespective of the specific configuration of the at least one fluidic connection as connection channel or as a common space not interrupted for example by an upward-running pillar, in particular not in the surface extension, the fluidic connection is characterized by the fact that it is limited upward by a ceiling region which is arranged below the flow channel—in other words, in a liquid-conductive connection, there is no direct perpendicular connection path to the flow channel—rather, the decontamination agent vapor has to ascend first laterally and then in the blind holes upward into the flow channel.

It has proven particularly expediently if a floor area or base surface of the fluidic connection, in particular of a connection channel, is configured as an evaporator surface heatable by the heating device so that decontamination agent vapor can already be generated thereon, wherein the decontamination agent vapor can ascend upward via the blind holes in each case neighboring the connection channel or connected via the flow channel. By means of this measure, the evaporation performance is further increased while maintaining a constant construction size. The evaporation performance within the fluidic region is particularly high due to this region being limited by the ceiling area.

It has proven particularly expedient if the fluidic connection, in particular an above-mentioned connection channel or the common connection space is produced from the solid, i.e. by material removal within a material block, in particular a high-grade steel block, in particular by milling in radial direction with respect to the longitudinal center axis of the blind holes. This can, for example, be realized in that a milling device is introduced into a blind hole and then is adjusted laterally, i.e. in radial direction toward the neighboring blind hole.

Leak tightness problems, as they could occur if the evaporator body is configured tray-like or in a two-piece structure in the region of the fluidic connection, can definitely be prevented by the configuration of the fluidic connection in a full material body. Thus, it is essential that the evaporator body, at least in the region of the fluidic connection is not configured multipart or does not have a joint or a junction but is configured as a full material block.

As explained, the upper edge of the blind holes is spaced perpendicular to the flow direction of the carrier medium in the flow channel between inlet and outlet by a full material region in which the blind holes are configured circumferentially closed. In view of the geometric configuration of the flow channel, there are different options. According to a first alternative, the flow channel comprises a planar bottom so that the blind hole edges of the blind holes connected to one another fluidically at a distance to the bottom, preferably of all blind holes, are arranged in a common plane. Alternatively and preferably, an embodiment can be realized in which the upper blind holes are not arranged in a common plane but in a bent bottom region of the flow channel. This embodiment allows for a bent, in particular cylindrical configuration of the flow channel which leads to more optimized flow conditions in the channel.

Also in view of the relative arrangement of two blind holes connected to one another fluidically, there are different alternatively, in particular however additionally realizable options. At least two blind holes connected to one another fluidically can be spaced from one another in direction of the flow direction of the carrier medium in the flow channel and/or perpendicular to this flow direction. Particularly preferably is at least a quad arrangement of blind holes in which the longitudinal center axes of the blind holes limit the corners of a virtual rectangle, preferably a square. In a quad arrangement, preferably each of the blind holes has a neighboring blind hole along the longitudinal extent of the flow channel as well as a neighboring blind hole perpendicular thereto. It is even further preferably if each of the blind holes is connected to the blind hole in the longitudinal extent of the flow channel as well as to the neighboring blind hole perpendicular thereto.

To further optimize the evaporation performance, it has proven advantageous to arrange the heating device not laterally offset to the longitudinal center axis or the center of a blind hole bottom, but in such a way that the virtual extensions of the respective blind hole longitudinal center axis intersect the heating device. Preferably, the heating device comprises at least one channel arranged in the evaporator body in which channel a resistance heating according to corresponding above definitions is arranged.

The invention also relates to a decontamination arrangement, comprising a space to be decontaminated, in particular an insulator and/or a lock and a device (rapid evaporator) configured according to the concept of the invention for generating decontamination agent vapor. The space is connected to the outlet of the flow channel of the rapid evaporator in a vapor-conductive manner. Preferably, air, in particular ambient air, is suctioned as carrier medium and introduced in the flow channel via the carrier medium inlet.

The invention also relates to a method for operating a device configured according to the concept of the invention for generating decontamination agent vapor, wherein liquid decontamination agent, in particular hydrogen peroxide, is supplied, preferably supplied dropwise, via the at least one supply channel in at least one of the blind holes. According to the invention it is provided that at least part of a liquid decontamination agent supplied to one of the blind holes flows in at least one other of the blind hole (connected to this blind hole in a fluidic manner) and there is evaporated to decontamination agent vapor. A higher operational safety results from this method as a greater, in particular the total evaporator surface is still at disposal even in case of failure of one supply channel.

In a further development of the invention, it is advantageously provided that also part of the liquid decontamination agent flowing in direction of a neighboring blind hole via the liquid-conductive connection is already evaporated in the fluidic connection, preferably in such a way that the emerging decontamination agent vapor, distributed to the directly connected blind holes, can flow upward in the flow channel. Additionally or as an alternative, it is provided that the liquid decontamination agent can flow in at least one further blind hole, which is in turn fluidically connected to the neighboring blind hole via a directly connected or fluidically connected blind hole.

It is more particularly preferably if the volume flow, i.e. the amount of the liquid decontamination agent supplied to the total number of blind holes per unit time, is held constant, in particular irrespective of the number of supply channels currently on disposal. This can be realized in that the speed of flow in the other supply channels automatically increases with constant volume flow, if one of the supply channels fails. In that the blind holes are fluidically-connected to one another at a distance to the flow channel, the liquid decontamination agent can optimally distribute and thereby a great evaporator surface is at disposal so that the operation of the rapid evaporator is not negatively influenced and the decontamination time does not need to be increased. Holding the volume flow constant, can be realized by a volume flow control wherefore a corresponding flow meter is arranged in a supply line for decontamination agent and a pump is controlled in such a way via control means connected to the flow meter in a signal-conductive manner that the volume flow is at least approximately held constant.

Further advantages, features and details result from the following description of preferred exemplary embodiments and by means of the drawings.

BRIEF DESCRIPTION OF THE DRAWINGS

The drawings show in.

The same elements and elements having the same function are denoted with the same reference characters throughout the figures.

DETAILED DESCRIPTION

FIG. 1 to FIG. 4 show an evaporator body 1 of full material, here high-grade steel. The evaporator body 1 forms the core constituent of a rapid evaporator otherwise not shown in detail and described for example in EP 2 488 602 B1 as well as a (decontamination) arrangement shown there in FIGS. 10 and 11.

A flow channel 2 is formed in the evaporator body 1 which connects a carrier medium inlet 3 to an outlet 4 in a gas-conducting manner. A flange 5, 6 is in each case assigned to the carrier medium inlet 3 and the outlet 4 with which the evaporator body 1 can be connected or flanged to corresponding lines or in the case of the outlet 4 directly to a space to be decontaminated, if need be. A carrier medium, in particular air is supplied via the carrier medium inlet 3 which medium then carries along the decontamination agent vapor emerging in the evaporator body 1 into the space to be decontaminated.

For the decontamination agent vapor generation per se, multiple, in the present example a total of four blind holes 7, 8, 9, 10 are provided, which are produced by drilling. An upper blind hole edge 11, 12, 13, 14 is located in a bent region of the cylindrically contoured flow channel below an upper opening 15 which is closed in a completely mounted rapid evaporator and which is penetrated by supply channels (not shown), in particular formed by injection grout needles, which permeate the flow channel 2 perpendicular to the longitudinal extent thereof and in each case end in one of the blind holes 7, 8, 9, 10. As described in the general description, it is not mandatory necessary, though preferred, to assign a distinct supply channel to each of the blind holes 7, 8, 9, 10 as the liquid decontamination agent, as will be described later, can/will be distributed at distance to the flow channel 2.

Below the blind holes 7, 8, 9, 10, reception bores 16, 17 running in parallel to the flow channel 2 are located which run directly below the blind holes 7, 8, 9, 10 and are intersected by virtual longitudinal center axes of the blind holes 7, 8, 9, 10. The heating device is received in the reception bores 16, 17 in the completely assembled rapid evaporator.

In each case a circumferentially closed blind hole section 18 adjoins the upper blind hole edge 11, 12, 13, 14 which section spaces respective neighboring of the blind holes. This blind hole section 18 comprising a circumferentially closed shell surface also spaces the flow channel 2 to fluidic connections 19 assigned thereto and which connect blind holes 7, 8, 9, 10 below the flow channel 2.

Figure 1:
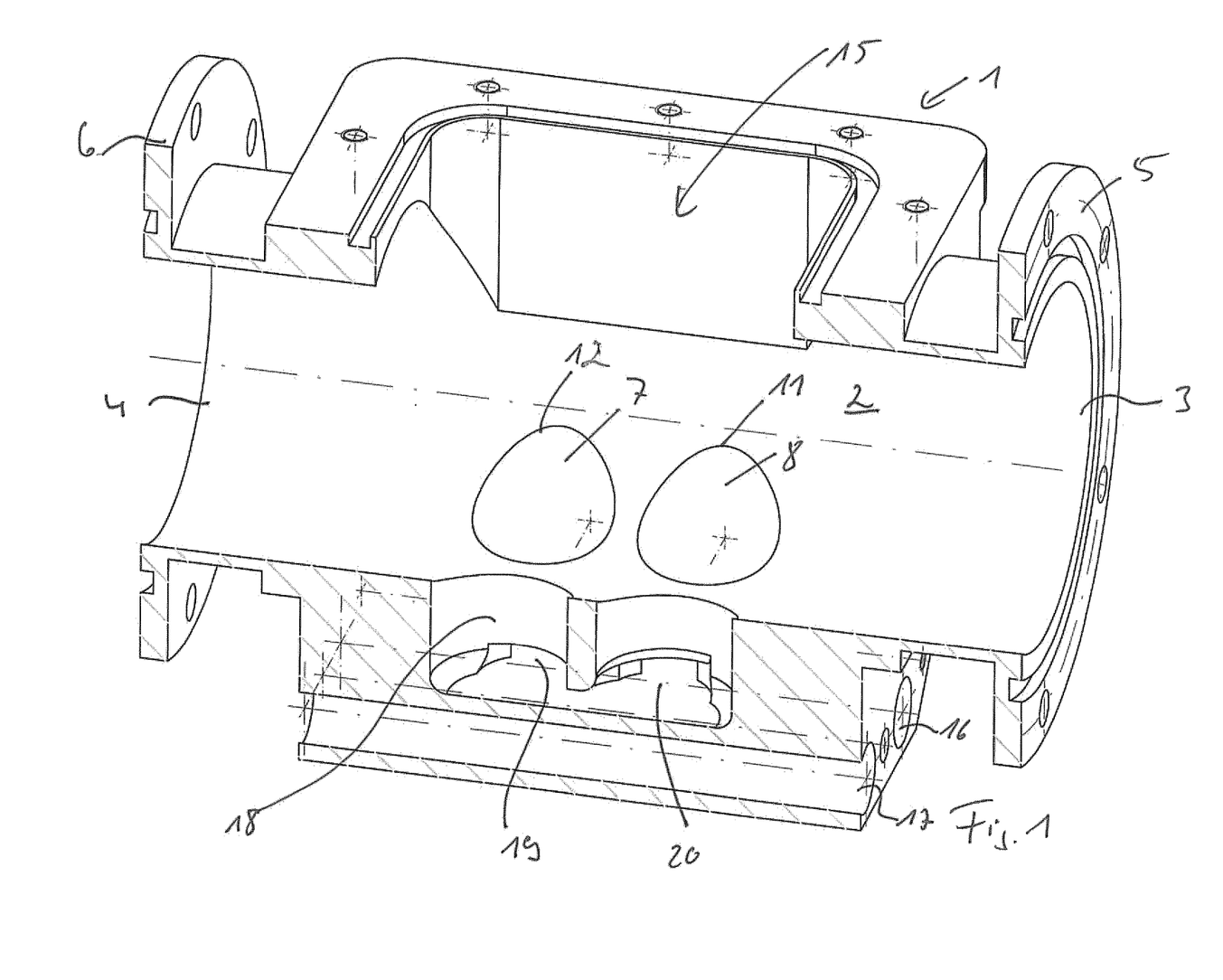
FIG. 1: a longitudinal sectional view through a single-part evaporator body of a rapid evaporator in a sectional plane running vertically.
Figure 2:
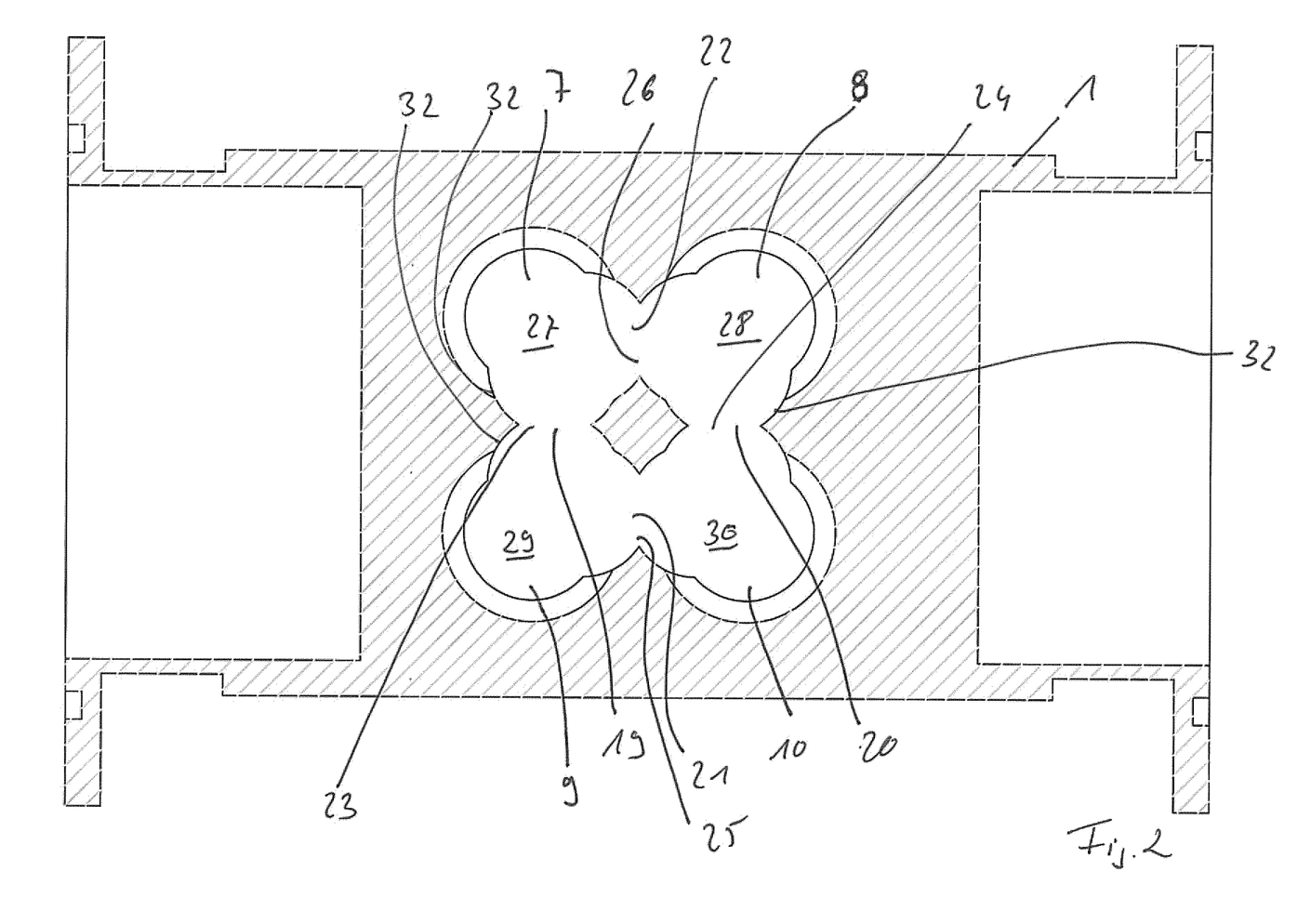
FIG. 2: a sectional view through the evaporator body according to FIG. 1 in a horizontal sectional plane.
Figure 3:
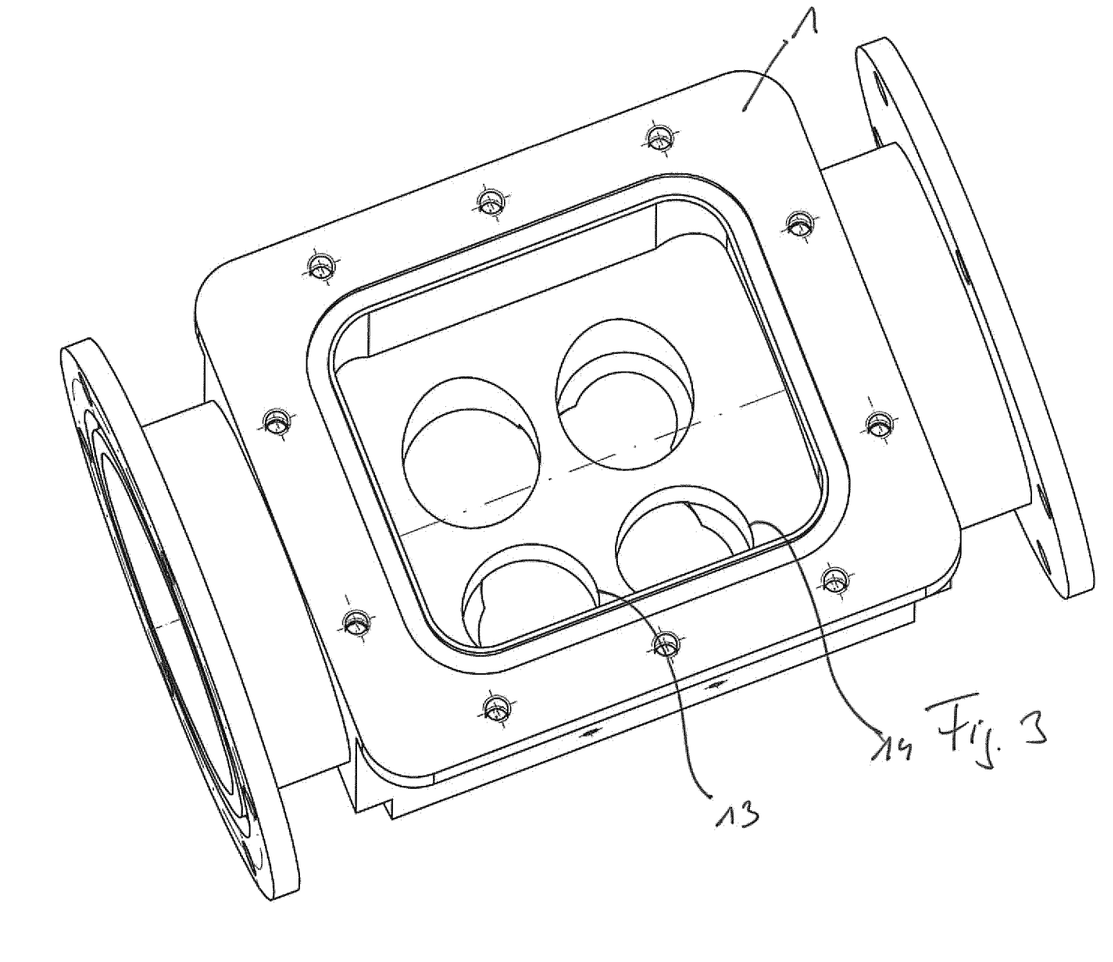
FIG. 3: a plan view on the evaporator body according to FIGS. 1 and 2, and FIG. 4: a sectional view through the evaporator body along a section line running essentially in a U-shape.

FIG. 1 shows two fluidic connections 19, 20 and FIG. 2 additionally shows the other fluidic connections 21, 22. In particular from FIG. 2 can be seen that the blind holes 7, 8, 9, 10, more specific the non-illustrated longitudinal center axes thereof, are arranged in a rectangular form or limit the corners of a virtual rectangular, here an virtual square, wherein each of the blind holes 7, 8, 9, 10 is connected to two further of the blind holes via in each case a fluidic connection.

It can be seen, that the fluidic connections 19, 20, 21, 22 (cf. in particular the synopsis of FIG. 1 and FIG. 2) are configured in each case as a circumferentially closed connection channel 1, i.e. as a type of connection tunnel. The fluidic connections 19, 20, 21, 22 or connection channels 1 have a (lowest) base 23, 24, 25, 26 which connects the lowest regions 27, 28, 29, 30 of the blind holes 7, 8, 9, 10, i.e. the blind hole bottoms to one another in a common plane.

Figure 4:
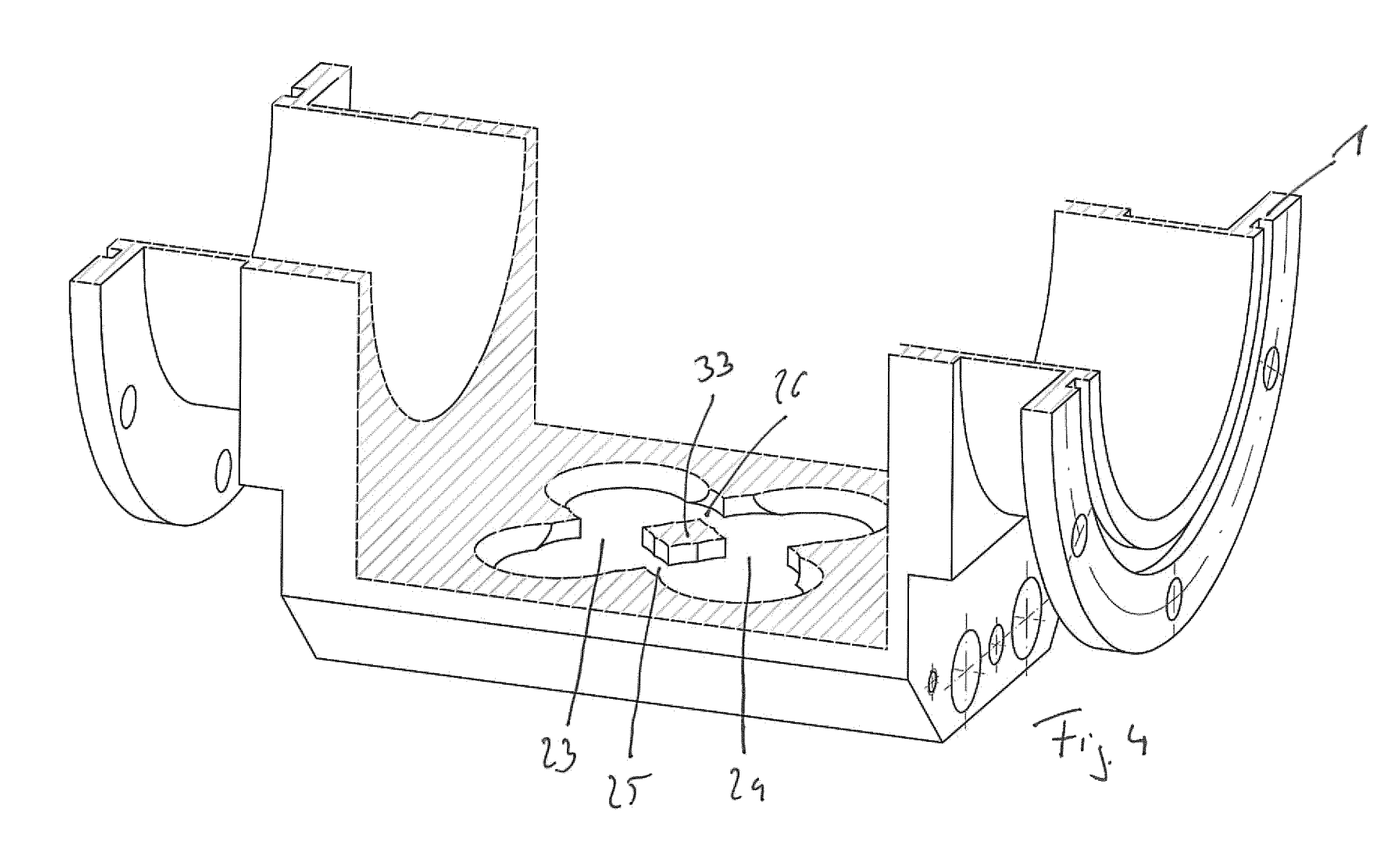

It can be seen in FIG. 4 how the fluidic connections 19, 20, 21, 22 or connection channels 1 are produced, namely by radial, i.e. lateral milling, starting from an original blind hole bore. The corresponding milling contours 32 can be seen in FIG. 4 and FIG. 2.

It can be taken in particular from FIGS. 2 and 4 that the blind holes arranged in a rectangle are separated from one another in a lower region, i.e. at one level with the fluidic connections 19, 20, 21, 22 via a center pillar 33 which establishes the connection between the evaporator body region laterally of the circumferentially closed blind hole sections 18 and the evaporator body region below the lowest regions 27, 28, 29, 30 of the blind holes 7, 8, 9, 10. In an alternative embodiment, a center pillar 33 can be omitted by removing the material forming the pillar, in particular by lateral milling, possibly when arranging the blind holes closer to one another. Then, a common interrupted space is established as the liquid-conductive connection between all of the blind holes. A such, the fluidic connection is also characterized by a ceiling region radially neighboring the blind holes.

The liquid decontamination agent introduced, in particular dropwise, in one of the blind holes 7, 8, 9, 10 via a supply channel, can distribute via the fluidic connections 19, 20, 21, 22 so that using the entire evaporator surface is possible even if intentionally or non-intentionally one of the blind holes 7, 8, 9, 10 is not directly supplied from above with liquid decontamination agent via a supply channel.

The configuration of the fluidic connections 19, 20, 21, 22 as in each case a circumferentially-closed connection channel means that these comprise a closed ceiling area with respect to the lower base 23, 24, 25, 26 as well as side wall areas spaced apart from one another and connecting the ceiling area to the base.

LIST OF REFERENCE CHARACTERS

1 Evaporator body
2 Flow channel
3 Carrier medium inlet
4 Outlet
5 Flange
6 Flange
7 Blind hole
8 Blind hole
9 Blind hole
10 Blind hole
11 Upper blind hole edge 12 Upper blind hole edge
13 Upper blind hole edge
14 Upper blind hole edge
15 Upper opening
16 Reception bore
17 Reception bore
18 Blind hole section
19 Fluidic connection
20 Fluidic connection
21 Fluidic connection
22 Fluidic connection
23 Base
24 Base
25 Base
26 Base
27 Lowest region
28 Lowest region
29 Lowest region
30 Lowest region
32 Milling edges
33 Pillar

The invention claimed is:

1. A device for generating decontaminating agent vapor, comprising a single- or multi-part evaporator body (1), a heating device for heating the evaporator body (1) as well as at least one supply channel for supplying a liquid decontaminating agent to be evaporated, to at least one of multiple blind holes (7, 8, 9, 10) arranged in the evaporator body (1), and to a flow channel (2) for a gaseous carrier medium arranged above upper blind hole edges (11, 12, 13, 14) of the multiple blind holes (7, 8, 9, 10) and connecting a carrier medium inlet (3) to an outlet (4) in a gas-conducting manner for discharging the decontaminating agent vapor through the outlet (4) in a flow direction of the gaseous carrier medium, wherein the flow channel is defined by a side wall, and the upper blind hole edges are defined in the side wall, wherein at least two of the multiple blind holes (7, 8, 9, 10) are connected to one another in a fluidic manner at a distance to their respective upper blind hole edges (11, 12, 13, 14) by fluidic connection (19, 20, 21, 22), and wherein a base of the fluidic connection (19, 20, 21, 22) is configured as an evaporator surface heatable by the heating device, so that decontaminating agent vapor generated thereon can ascend into the flow channel (2) via the at least two of the multiple blind holes (7, 8, 9, 10) connected to one another by means of the fluidic connection (19, 20, 21, 22), and wherein the fluidic connection (19, 20, 21, 22) is configured such that the fluidic connection (191, 20, 21, 22) connects a deepest region (27, 28, 29, 30) of each of the at least two of the multiple blind holes (7, 8, 9, 10), which are connected to one another in fluidic manner, in a common plane, and wherein the fluidic connection (19, 20, 21, 22) is at least partially defined by a surface in the common plane at the deepest region (27, 28, 29, 30).

2. The device according to claim 1, wherein the fluidic connection (19, 20, 21, 22) comprises a circumferentially closed connection channel in the single- or multi-part evaporator body (1).

3. The device according to claim 2, wherein the circumferentially closed connection channel is between two blind holes (7, 8, 9, 10) fluidically connected to one another.

4. The device according to claim 1, wherein the fluidic connection (19, 20, 21, 22) is produced by milling high-grade steel in radial direction with respect to longitudinal center axes of the multiple blind holes (7, 8, 9, 10).

5. The device according to claim 1, wherein the upper blind hole edges (11, 12, 13, 14) of the multiple blind holes (7, 8, 9, 10) fluidically connected to one another are arranged in a common plane.

6. The device according to claim 5, wherein the upper blind hole edges (11, 12, 13, 14) of all blind holes (7, 8, 9, 10) fluidically-connected to one another are arranged in the common plane.

7. The device according to claim 1, wherein the upper blind hole edges (11, 12, 13, 14) are defined in and located on a bent, cylindrical shell surface section of the side wall defining the flow channel (2).

8. The device according to claim 7, wherein the upper blind hole edges extend laterally up along a curved inner surface of the bent, cylindrical shell surface section, away from bottom dead center of the flow channel (2), and the upper blind hole edges of the multiple blind holes are defined on either side of, and spaced from, a section of the side wall extending along bottom dead center of the flow channel.

9. The device according to claim 1, wherein at least two of the multiple blind holes (7, 8, 9, 10) fluidically connected to one another are arranged to be spaced apart in the direction of the flow direction of the gaseous carrier medium and/or wherein at least two of the multiple blind holes (7, 8, 9, 10) fluidically connected to one another are arranged to be spaced apart perpendicular to the flow direction of the gaseous carrier medium.

10. The device according to claim 1, wherein the heating device is arranged in the single- or multi-part evaporator body (1) directly below each blind hole bottom in a virtual extension of a respective blind hole longitudinal center axis.

11. The device according to claim 1, wherein the decontaminating agent vapor is hydrogen peroxide vapor and the gaseous carrier medium is air.

12. The device according to claim 1, wherein the at least one supply channel comprises multiple supply channels.

13. The device according to claim 1, wherein all multiple blind holes (7, 8, 9, 10) are connected to one another in a fluidic manner at a distance to their respective upper blind hole edges (11, 12, 13, 14).

14. The device according to claim 1, wherein the fluidic connection has a planar base surface.

15. Arrangement, comprising a space to be decontaminated and a device according to claim 1 by means of which the space can be applied with decontaminating agent vapor.

16. The arrangement according to claim 15, wherein the space is an isolator and/or a lock.

17. A method for operating a device for generating decontaminating agent vapor, according to claim 1, wherein liquid decontamination agent is supplied dropwise via the at least one supply channel into at least one of the blind holes (7, 8, 9, 10), wherein liquid decontamination agent supplied into one of the multiple blind holes (7, 8, 9, 10) flows into at least another one of the multiple blind holes (7, 8, 9, 10) and is evaporated into liquid decontamination agent vapor there.

18. The method according to claim 17, wherein part of the liquid decontamination agent flowing through the fluidic connection (19, 20, 21, 22) evaporates in the fluidic connection (19, 20, 21, 22) and/or wherein part of the liquid decontamination agent flowing through the fluidic connection (19, 20, 21, 22) flows to yet a further blind hole (7, 8,

9, 10) via the other blind hole (7, 8, 9, 10) and a further fluidic connection (19, 20, 21, 22).

19. The method according to claim 17, wherein the total volume flow of the liquid decontamination agent supplied to the evaporator body (1) is kept constant.

\* \* \* \* \*